US010835778B2

(12) United States Patent
Kaji et al.

(10) Patent No.: US 10,835,778 B2
(45) Date of Patent: Nov. 17, 2020

(54) MOTION CAPTURE SYSTEM, MOTION CAPTURE PROGRAM AND MOTION CAPTURE METHOD

(71) Applicant: LEOMO, Inc., Boulder, CO (US)

(72) Inventors: Kunihiko Kaji, Tokyo (JP); Satoru Taniyama, Tokyo (JP); Shinichi Fukuma, Tokyo (JP)

(73) Assignee: LEOMO, Inc., Boulder, CO (US)

( * ) Notice: Subject to any disclaimer, the term of this patent is extended or adjusted under 35 U.S.C. 154(b) by 0 days.

(21) Appl. No.: 16/424,486

(22) Filed: May 29, 2019

(65) Prior Publication Data
US 2019/0275372 A1   Sep. 12, 2019

Related U.S. Application Data

(63) Continuation of application No. PCT/JP2016/085627, filed on Nov. 30, 2016.

(51) Int. Cl.
*A63B 24/00* (2006.01)
*G06F 3/01* (2006.01)
(Continued)

(52) U.S. Cl.
CPC ........ *A63B 24/0003* (2013.01); *A61B 5/1114* (2013.01); *A61B 5/1122* (2013.01);
(Continued)

(58) Field of Classification Search
CPC ....... A61B 5/11; A61B 5/1112; A61B 5/1116; A61B 5/1118; A61B 5/112; A61B 5/1122;
(Continued)

(56) References Cited

U.S. PATENT DOCUMENTS 6,876,947 B1* 4/2005 Darley ................ A43B 3/0005
702/160
8,961,439 B2* 2/2015 Yang .................... A61B 5/1038
600/595
(Continued)

FOREIGN PATENT DOCUMENTS

AT         505617 A    3/2009
DE        4227586 A    2/1994
(Continued)

OTHER PUBLICATIONS

Google Patent English translation of the Kitawaki reference (JP 2014/008789 A) (Year: 2014).*
(Continued)

*Primary Examiner* — Joshua Lee
(74) *Attorney, Agent, or Firm* — Yokoi & Co., U.S.A.; Toshiyuki Yokoi

(57) ABSTRACT

Display and output are performed in such a manner as to allow complex body motions to be comprehended instantaneously. There are provided: a plurality of body motion sensors 40 which are worn on a wearer's 1 parts subject to cyclic motions and which are capable of measuring three-dimensional displacements and accelerations at the respective parts; a memory 114 which records detection results as body motion data; a cycle extraction unit 170c which extracts a cyclic motion of each of the body motion sensors 40 on the basis of accumulated body motion data; an analysis unit 170d which analyzes the characteristic of a change in angular velocity in the extracted cyclic motion; and displays 100a, 100b that display or output the characteristic analyzed by the analysis unit 170d in association with the rotation angle of the cyclic motion extracted by the cycle extraction unit 170c.

15 Claims, 12 Drawing Sheets

(51) Int. Cl.
*A61B 5/11* (2006.01)
*A61B 5/22* (2006.01)
*A61B 5/00* (2006.01)

(52) U.S. Cl.
CPC ............ *A61B 5/221* (2013.01); *A61B 5/6807* (2013.01); *A63B 24/0062* (2013.01); *G06F 3/011* (2013.01); *G06F 3/017* (2013.01); *A61B 5/6838* (2013.01); *A61B 2503/10* (2013.01)

(58) Field of Classification Search
CPC ........ A61B 2562/0219; A63B 24/0003; A63B 24/0062; G04G 17/08; G04G 21/025; G04G 21/04; G06F 1/16; G06F 1/163; G06F 1/1686; G06F 1/1698; G06F 3/011; G06F 3/017; G06F 3/03547; G06F 3/041; G06F 3/0488
See application file for complete search history.

(56) References Cited

U.S. PATENT DOCUMENTS

| | | | |
|---|---|---|---|
| 9,067,097 B2* | 6/2015 | Lane | G06K 9/00342 |
| 9,622,686 B1* | 4/2017 | Berme | A61B 5/112 |
| 9,968,840 B2* | 5/2018 | Czaja | A63C 11/003 |
| 10,065,074 B1* | 9/2018 | Hoang | G16H 40/63 |
| 10,286,313 B2* | 5/2019 | Goetgeluk | A63F 13/40 |
| 2010/0305480 A1 | 12/2010 | Fu et al. | |
| 2011/0111923 A1 | 5/2011 | Bacanovic et al. | |
| 2011/0166821 A1* | 7/2011 | Kim | A63B 69/0022 |
| | | | 702/141 |
| 2013/0006583 A1* | 1/2013 | Weast | A61B 5/112 |
| | | | 702/189 |
| 2013/0041617 A1 | 2/2013 | Pease et al. | |
| 2014/0228989 A1 | 8/2014 | Tagliabue | |
| 2014/0278218 A1* | 9/2014 | Chang | G01P 15/00 |
| | | | 702/150 |
| 2016/0322078 A1* | 11/2016 | Bose | G11B 27/031 |
| 2016/0375346 A1* | 12/2016 | Czaja | A63C 11/003 |
| | | | 434/253 |
| 2017/0168555 A1* | 6/2017 | Munoz | G06F 1/3228 |

FOREIGN PATENT DOCUMENTS

| | | |
|---|---|---|
| JP | 2010-536508 A | 12/2010 |
| JP | 2013-215590 A | 10/2013 |
| JP | 2014-008789 A | 1/2014 |
| JP | 2014-504943 A | 2/2014 |
| WO | 2016/035884 A | 3/2016 |

OTHER PUBLICATIONS

International Search Report for PCT/JP2016/085627 dated Feb. 21, 2017.
PCT written opinion dated Feb. 21, 2017.
Japanese notice of reason for refusal dated Jan. 9, 2018.
Japanese notice of reason for refusal dated Aug. 7, 2018.
Japanese decision to grant a patent dated Jan. 8, 2019.
Pioneer Corp., 'Pedaling Monitor System', Pioneer, Pioneer Corp., Mar. 31, 2014.
Extended European Search Report dated Oct. 2, 2019.

* cited by examiner

MOTION CAPTURE SYSTEM, MOTION CAPTURE PROGRAM AND MOTION CAPTURE METHOD

TECHNICAL FIELD

The present invention relates to a motion capture system, a motion capture program and a motion capture method making use of a so-called smartphone, and wearable type and another type information terminal device.

BACKGROUND ART

In recent years, along with the advent of the miniaturization, weight saving and multifunction of the information terminal device, wearing type information processing terminals, i.e., so-called wearable terminals are becoming spread, and such a wearable terminal is lightweight and provided with a clock function, a GPS function and other functions such as a communication function to perform communication with various sensors such as a heart rate sensor, so that systems have been developed which can be worn during running, walking, sports training or exercise such as riding a cycle for recording or monitoring body motion (for example, refer to Patent Document 1).

In accordance with the system disclosed in this Patent Document 1, it is possible to provide realtime feedback data to a user during exercise by installing a device for measuring motion parameters in a footwear sole of the user, comparing motion parameters obtained during monitoring the exercising user with basic baseline data, and changing playback music or the like in accordance with whether or not the result of comparison falls in an allowable range.

PRIOR ART DOCUMENTS

Patent Documents

[Patent Document 1] Japanese Patent Published Application No. 2013-215590

SUMMARY OF THE INVENTION

Problems to be Solved by the Invention

However, since the human body motion includes complicated movements of movable sections which are digitalized with a number of parameters, it is desirable to provide a user interface for displaying changes of the number of motion parameters to a user during an athletic activity. Particularly, in the case where coaching is conducted on the basis of the result of capturing body motion during exercise on a real time base, parameters converted on a real time base must be displayed in such a manner as to allow a user to comprehend instantaneously.

In order to solve the problem as described above, it is an object of the present invention to provide a motion capture system, a motion capture program and a motion capture method in which, when capturing exercise of the body of a user in a system, complicated body motions are displayed and output so as to allow the body motions to be comprehended instantaneously.

Means for Solving Problem

In order to accomplish the object as described above, the present invention is related to a motion capture system which detects body motions of a wearer comprising:

a plurality of body motion sensors which are worn on parts of the body of the wearer, which are cyclically moved, so that three-dimensional displacement and acceleration of each of the parts can be measured;

a body motion recording unit which records detection results of the body motion sensors as body motion data;

a cycle extraction unit which extracts a cyclic motion of each of the body motion sensors on the basis of the body motion data accumulated in the body motion recording unit;

a characteristic analysis unit which detects a characteristic of angular velocity variation of the cyclic motion extracted by the cycle extraction unit;

an output device which displays or outputs the characteristic analyzed by the characteristic analysis unit in correspondence with the rotation angle of the cyclic motion extracted by the cycle extraction unit.

Also, the present invention is related to a motion capture method which detects body motions of a wearer comprising:

a body motion recording step of measuring, with body motion sensors which are worn on parts of the body of the wearer which are cyclically moved, three-dimensional displacement and acceleration of each of the parts, and recording detection results of the body motion sensors as body motion data;

a cycle extraction step of extracting, with a period extraction unit, a cyclic motion of each of the body motion sensors on the basis of the body motion data accumulated in the body motion recording unit;

a characteristic analysis step of analyzing, with a characteristic analysis unit, a characteristic of angular velocity variation of the cyclic motion extracted in the cycle extraction step;

an output step of displaying or outputting, with an output device, the characteristic analyzed in the characteristic analysis step in correspondence with the rotation angle of the cyclic motion extracted in the cycle extraction step.

In accordance with these invention, it is possible to instantaneously comprehend the occurrence of the disturbance of a form and the collapse of a rhythm when stepping on the pedal of a bicycle by detecting a body motion for example a cyclic motion such as pedaling a bicycle and displaying or outputting characteristics of the cyclic motion in association with the rotation angle.

In the invention as described above, it is preferred that the body motion sensors are worn on parts located below both ankles of the wearer. In this case, for example, the body motion sensor can be located on a footwear such as an athletic shoe which is worn below an ankle so that the body motion sensor can be worn together with the footwear, and therefore the body motion sensor can easily be worn.

Also, in the invention as described above, it is preferred that the output device displays a plane circle as the cyclic motion extracted by the cycle extraction unit, and displays a central angle of this plane circle as the rotation angle at which the characteristic analyzed by the characteristic analysis unit appears. In this case, the output device displays the strength of the characteristic analyzed by the body motion sensor in correspondence with the distance from the origin of the plane circle. Also, in this case, the output device displays the variation of the characteristic analyzed by the body motion sensor with a symbol, a figure and a color or size thereof. In this case, it is possible to geometrically express cyclic motions such as pedaling a bicycle in accordance with the rotation angles thereof and comprehend the characteristics of the cyclic motions at first sight.

Effects of the Invention

As has been discussed above, in accordance with this invention, a system which captures exercise of the body of a user, displays and outputs complicated body motions so as to allow the body motions to be comprehended instantaneously, and it is possible to analyze the mutual influence among parameters of an exercise form and appropriately adjust deformation of the exercise form. Particularly, in accordance with the present invention, since the body motion sensor can be freely worn in an arbitrary position and an arbitrary direction, usability can be improved.

Incidentally, the motion capture system and the motion capture method in accordance with the present invention as described above can be implemented in a computer by running the motion capture program of the present invention described in a predetermined language. Namely, the system having the functionality as described above can be built to implement the motion capture method by installing the program of the present invention in an IC chip or a memory device of a mobile terminal device, a smartphone, a wearable terminal, a mobile PC, another type information processing terminal, or a general purpose computer such as a personal computer or a server computer, and running the program on the CPU.

The motion capture program in accordance with the present invention as described above can be distributed, for example, through a communication line, or as a package application which can be run on a stand-alone computer by storing the program in a storage medium which can be read by a computer. Specifically, such a storage medium includes a magnetic recording medium such as a flexible disk or a cassette tape, an optical disc such as CD-ROM or DVD-ROM, a RAM card and a variety of storage mediums. In addition, in accordance with the computer readable medium in which this program is stored, the above system and method can be easily implemented with a general purpose computer or a dedicated computer, and the program can be easily maintained, transported and installed.

MODE FOR CARRYING OUT THE INVENTION

In what follows, an embodiment of the present invention will be explained with reference to the accompanying drawings. The present embodiment provides a system which makes it possible to perform measurement and coaching for multiple-stage competition such as triathlon involving cycling and running by the use of a single information terminal device 100. Incidentally, the embodiment described below has been disclosed with devices and the like by way of illustration for implementing the technical idea of the present invention, which is not limited to the material, formation, structure, arrangement of each constituent member as described below. The technical idea of the present invention can be modified within the scope of claims.

(System Configuration)

Figure 1:
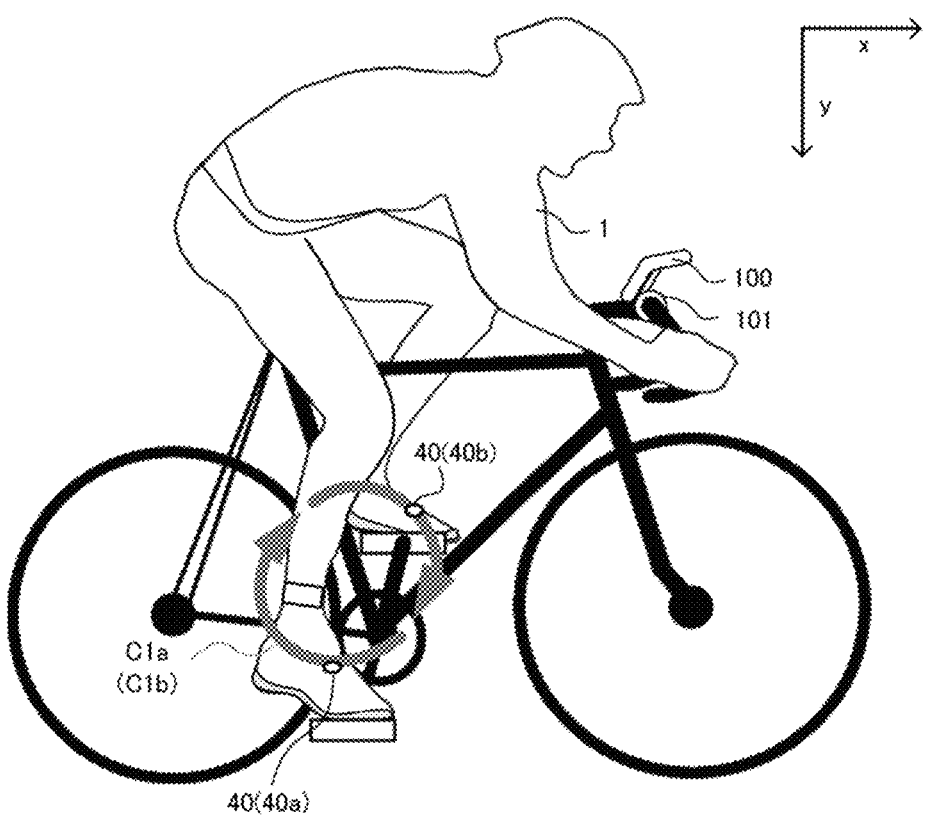
FIG. 1 is an explanatory view for showing the usage of a motion capture system in accordance with an embodiment.
Figure 2:
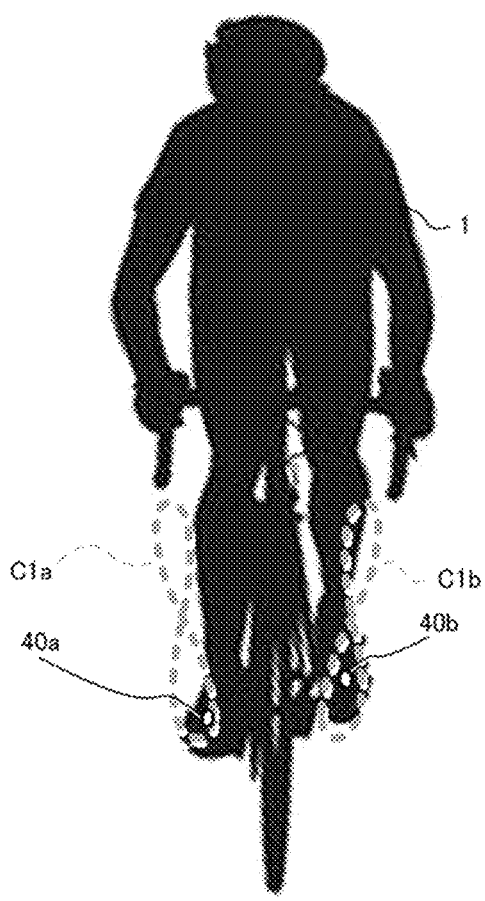
FIG. 2 shows one example of body motion reproduction data which is acquired in accordance with the embodiment.

FIG. 1 is an explanatory view for showing the usage of a motion capture system with the information terminal device 100 in accordance with the present embodiment. FIG. 2 shows one example of body motion reproduction data which is acquired by the motion capture system in accordance with the present embodiment. Also, FIG. 3 is a block diagram for showing the internal structure of the respective devices.

Figure 3:
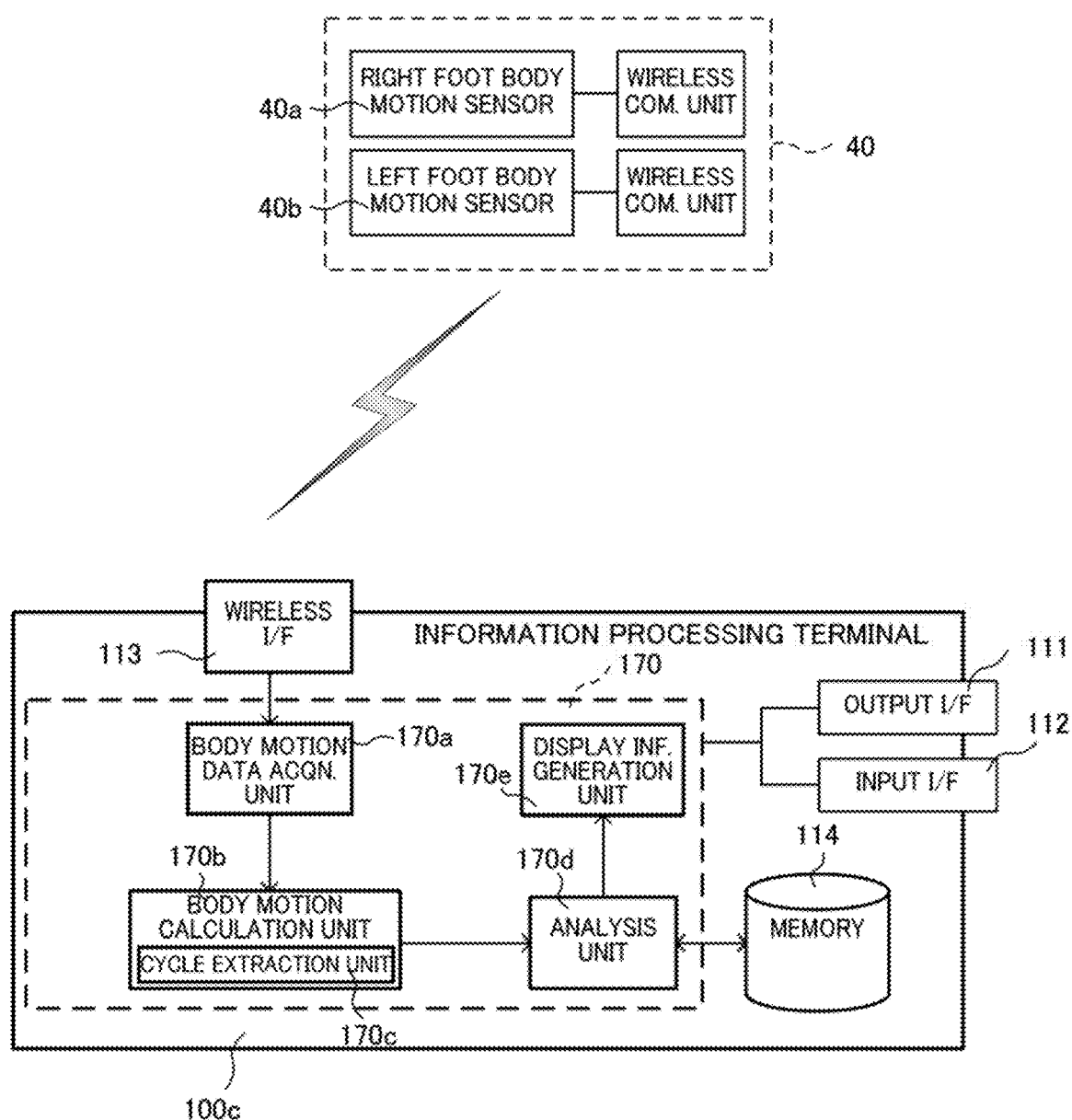
FIG. 3 is a block diagram for showing the internal structure of the respective devices in accordance with the embodiment.

As illustrated in FIG. 1 and FIG. 3, the motion capture system in accordance with the present embodiment includes the information terminal device 100 worn on a wearer 1, and a body motion sensors 40 (40a and 40b) worn on parts of the wearer and connected to the information terminal device 100 through wireless connection. Meanwhile, in the case of the present embodiment, a system can basically be implemented within an area where short range wireless communication is available between the information terminal device 100 and the body motion sensors 40. The system is not connected to a server or the like on the communication network during actual measurement, and can be operated offline in a so-called stand-alone configuration.

(Structure of Each Device)

(1) Body Motion Sensors

The body motion sensors 40a and 40b are a pair of sensors which are worn on the wearer's 1 parts subject to cyclic motions to detect the three-dimensional displacement and acceleration of each part. In the case of the present embodiment, the body motion sensors 40a and 40b are worn on parts located below both ankles of the wearer 1, and include a right foot body motion sensor 40a worn on the right instep of the wearer and a left foot body motion sensor 40b worn on the left instep of the wearer. Each of the motion sensors 40a and 40b incorporates a three-axis acceleration meter for measuring the acceleration of an object, a three-axis gyroscope for measuring the angular speed of the object, a three-axis magnetic sensor for measuring the magnitude and direction of a magnetic field, so that motions about nine axes can be detected.

Each motion sensor 40 can be detachably worn on the shoes of a wearer or the like with a clip or the like member, and the wearer can attach and detach each sensor for measurement in the feelings of daily life when putting on or taking off shoes, so that it is possible to perform continuous measurement without putting burdens on the wearer.

Each of these body motion sensors 40 (the body motion sensors 40a and 40b) is provided with a wireless communication unit as illustrated in FIG. 3. This wireless communication unit incorporates an antenna and can perform a communication process with the information terminal device 100 by the function to perform short range wireless communication on the basis of a data communication protocol such as BTLE (Bluetooth (registered trademark) Low Energy, Bluetooth (registered trademark) 4.0). Meanwhile, while the wireless communication unit of each body motion sensor 40 uses BTLE as a low power consumption communication protocol in the case of the present embodiment, ANT, ANT+ or the like protocol can be employed instead. Alternatively, standard Bluetooth (registered trademark) can be employed instead.

Figure 9A:
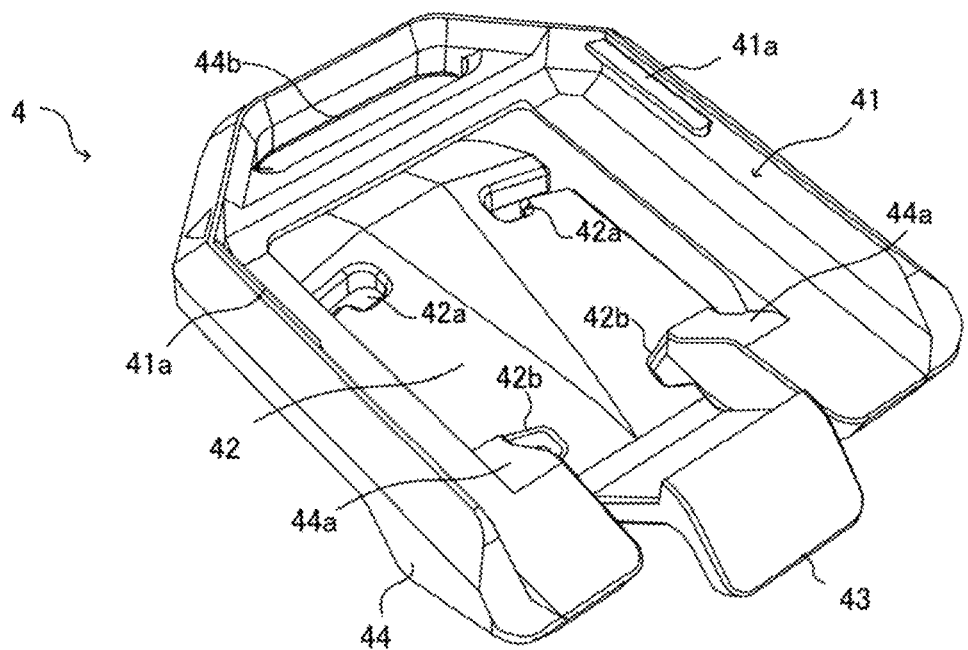
FIGS. 9A and 9B are perspective views for showing the overall configuration of a clip used for attaching a body motion sensor in accordance with the embodiment.
Figure 9B:
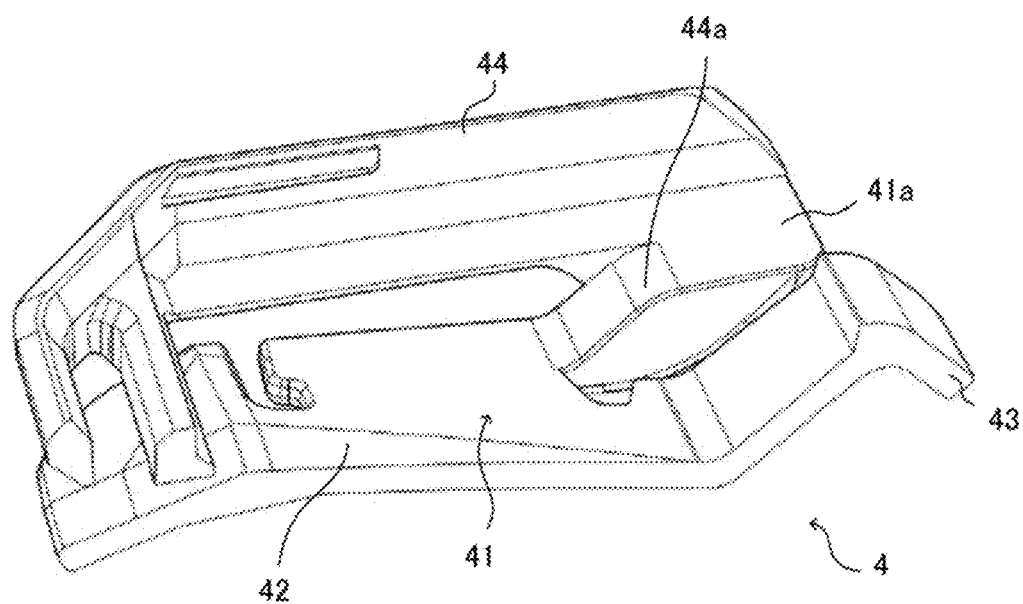
Figure 10A:
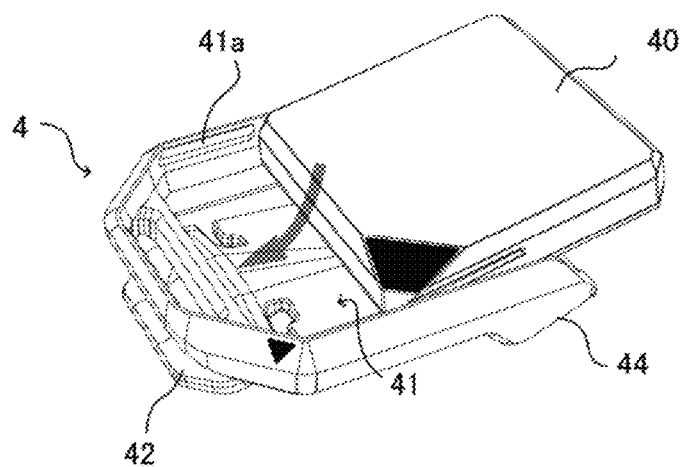
FIGS. 10A and 10B are perspective views for showing the operation of mounting the body motion sensor on the clip in accordance with the embodiment.
Figure 10B:
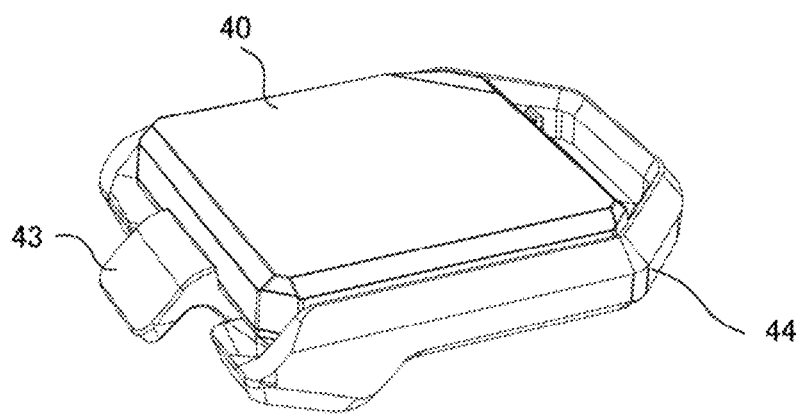

Next, a clip 4 used for wearing the body motion sensors 40a and 40b on the body of the wearer 1 will be explained. FIGS. 9A and 9B are a perspective view and a cross sectional view for showing the overall configuration of the clip 4 used to attach the body motion sensor 40 in accordance with the present embodiment. FIGS. 10A and 10B are perspective views for showing the operation of mounting the body motion sensor 40 on the clip 4. Incidentally, the body motion sensors 40a and 40b in accordance with the present embodiment are fixed to shoes for bicycle with a clip or the like. The shoes are fixed to clipless pedals for ordinary bicycle during exercise through cleats for clipless pedals which are attached to the shoes.

Figure 11:
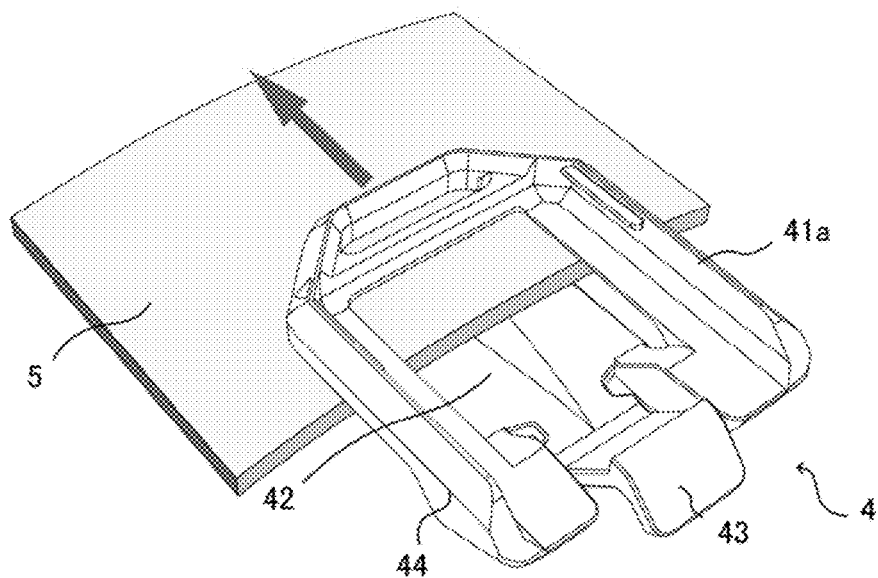
FIG. 11 is a perspective view for showing the operation of attaching the clip of the embodiment to another part.

Each body motion sensor 40 can easily be attached to a clothing, shoes or the like of a wearer through the clip 4 by mounting the body motion sensor 40 on the clip 4. Specifically, the clip 4 is an instrument which is detachably attached to grooves of the body motion sensor 40 and provided with a gripping member 42 with which the clip 4 can be attached to a clothing or the like of a wearer together with the body motion sensor 40 mounted thereon. This gripping member 42 is a tongue-like member which is projected in the bottom side of a rectangular main body frame 44 and integrally formed through the connection member 44a which is part of a concave portion 41 formed of the main body frame 44. And, this gripping member 42 is supported in parallel with the bottom of the main body frame 44 by the elastic force of the connection member 44a in order to grip another part such as an edge of a clothing between the gripping member 42 and the bottom of the main body frame 44 as illustrated in FIG. 11.

Also, at the rear end of the main body frame 44, a stopper 43 is formed to fix the body motion sensor 40 which is fitted into the concave portion 41. This stopper 43 serves as a fix member for fixing the body motion sensor 40, which is fitted into the concave portion 41, and is continuously formed with the gripping member 42 to fix the body motion sensor 40 under pressure by the reaction force of the gripping member 42 gripping another part. Specifically describing, the stopper 43 is formed integrally with the rear end of the gripping member 42, and connected to the main body frame 44 through the connection member 44a formed on the concave portion 41 of the main body frame 44. When the gripping member 42 is pushed down against the elastic force of the connection member 44a away from the main body frame 44, the stopper 43 rises. Conversely, when the stopper 43 is pushed down, the gripping member 42 exerts a gripping force. Then, the concave portion 41 is provided with flange portions 41a to be fitted into grooves which are provided at both sides of the body motion sensor 40. And, when the body motion sensor 40 is mounted on the clip, as illustrated in FIGS. 10A and 10B, the flange portions 41a are inserted into the grooves so that the body motion sensor 40 slides into and fits on the concave portion 41 in the direction of an arrow shown in the figure.

Since the stopper 43 is urged to push forward the rear end of the body motion sensor 40 fitting on the concave portion 41, the flange portions 41a and the grooves are firmly engaged and fixed together. When another part 5 such as an edge of a clothing is gripped between the gripping member 42 and the bottom of the main body frame 44 with this body motion sensor 40 fitting on the concave portion 41, the gripping member 42 is pushed down against the elastic force of the connection member 44a away from the main body frame 44, and the stopper 43 rises so that the body motion sensor 40 is more firmly fixed. Incidentally, when the body motion sensor 40 is dismounted from the clip 4, the clip 4 is detached from the part 5 gripped between the gripping member 42 and the bottom of the main body frame 44 so that the engaging force of the stopper 43 is lessened to make it easy to push down the stopper 43, and the flange portions 41a can be removed from the grooves so that the body motion sensor 40 can easily be dismounted from the clip 4.

Figure 12:
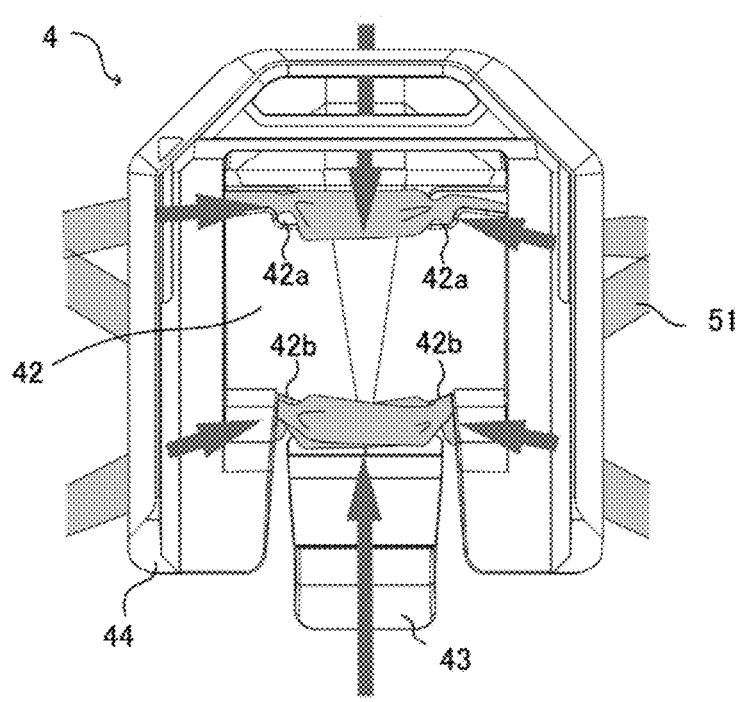
FIG. 12 is a perspective view for showing the operation of attaching the clip of the embodiment to another part by the use of a string member.

Furthermore, the clip 4 is provided with a fastening mechanism, for example, for engaging the clip 4 with a fastening member such as a shoelace of an athletic shoe to fasten the clip 4 with a part such as the shoelace. FIG. 12 is a perspective view for showing the operation of attaching the clip 4 of the present embodiment to another part.

Specifically, as illustrated in FIG. 9, cut portions 42a, 42b and 42b are formed through edges of both sides of the gripping member 42. This clip 4 can be fastened to the upper side of an athletic shoe, i.e., the upper instep of each foot of the wearer by hooking a fastening member such as a shoelace 51 inserted between the lower surface of the main body frame 44 and the gripping member 42 as illustrated in FIG. 12. The body motion sensor 40 can thereby easily be worn on the body of the wearer by mounting the body motion sensor 40 on the clip 4 fastened to the upper side of an athletic shoe. Also, the body motion sensor 40 can easily be dismounted from the clip 4 by pushing down the stopper 43. Meanwhile, the main body frame 44 is provided at its front end with an engagement hole 44b through which a string or a strap can be fastened. Another fastening member may be fastened by the use of this engagement hole 44b.

(2) Information Terminal Device

Figure 4A:
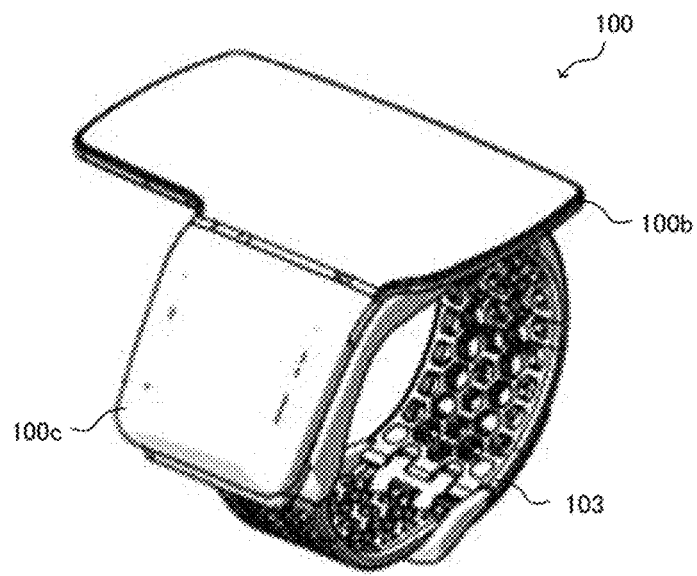
FIGS. 4A and 4B are explanatory views for showing an information terminal device in accordance with the embodiment, including a perspective view 4A for showing the information terminal device in accordance with the embodiment (a large display is installed) and an explanatory view 4B for showing the usage thereof.
Figure 4B:
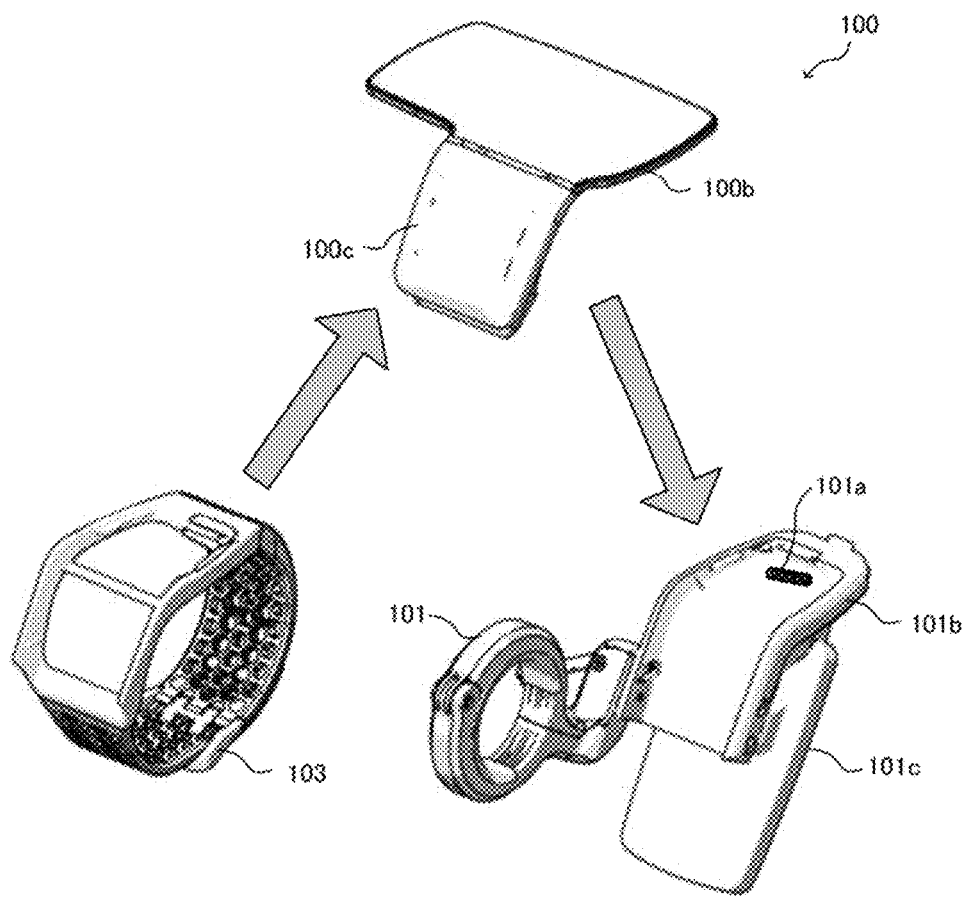
Figure 5A:
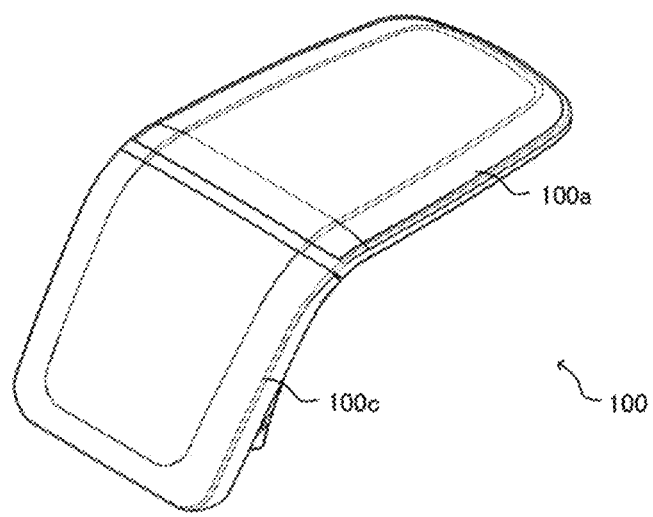
FIGS. 5A and 5B include a perspective view 5A for showing the information terminal device in accordance with the embodiment (a small display is installed) and an explanatory view 5B for showing the usage thereof.
Figure 5B:
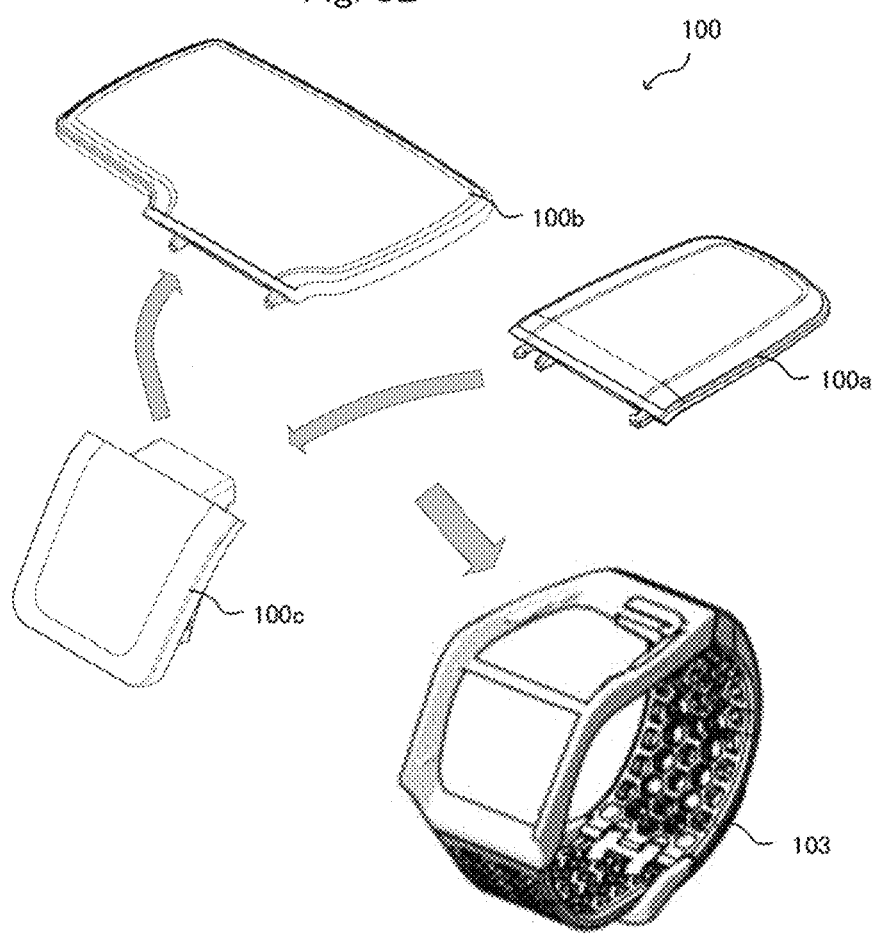
Figure 6A:
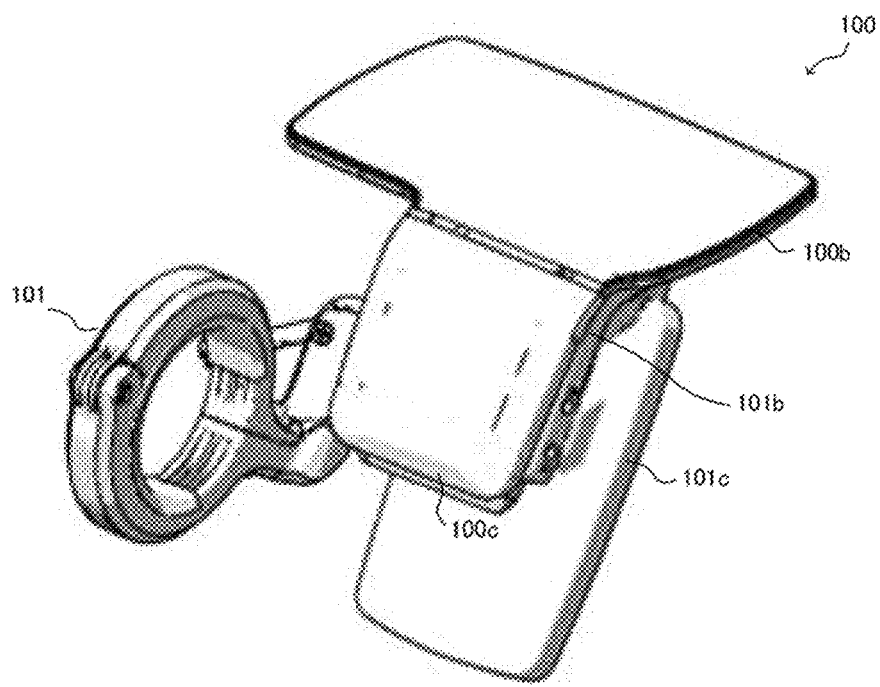
FIGS. 6A and 6B include a perspective view 6A for showing the information terminal device in accordance with the embodiment mounted on a mount device and an explanatory view 6B for showing the usage thereof.
Figure 6B:
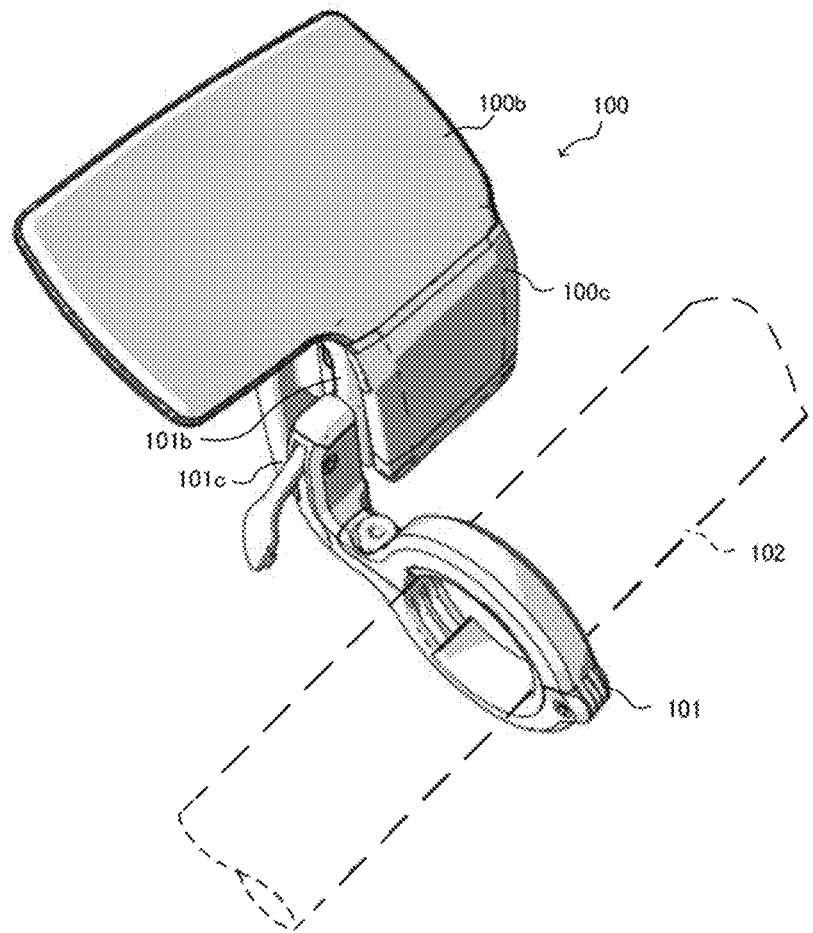

FIG. 4A to FIG. 6B show the overall configuration and usage of an information terminal device in accordance with the present embodiment. The information terminal device 100 in accordance with the present embodiment is configured as a wrist watch type wearable terminal which can be worn by a user with a belt member 104, as illustrated in FIGS. 4A, 4B and FIGS. 5A, 5B, and configured to be mounted on the handlebar of a bicycle or the like as illustrated in FIG. 6A, 6B.

More specifically describing, as illustrated in FIG. 4B, the information terminal device 100 is configured to be selectively united with a belt member 104 or a docking type device 101b. The information terminal device 100 and the docking type device 101b or the belt member 104 are configured to be attached to and removed from each other, and can be separated and joined if necessary. Also, there are many types of the information terminal device 100 and docking type device 101b which have different additional functions and designs in accordance with using purposes respectively, and can be arbitrarily selected and freely combined for the purposes. For example, as illustrated in FIG. 4B and FIGS. 6A, 6B, the docking type device 101b to be joined to the information terminal device 100 can be connected to a mount device 101 for mounting the docking type device 101b on the handlebar of a bicycle, and the power supply device 101c which is a battery as an extension.

Also, in the case of the present embodiment, the information terminal device 100 can be worn on an arm of a user with the belt member 104 as the wearing type terminal in the form of a wristband, and mounted on the handlebar 102 of a bicycle with a clamp of the mount device 101, and it is possible to continuously utilize a single (a type of) information terminal device for both cycling and running, and continuously and seamlessly utilize the sensors worn on a human body for both cycling and running without removing the sensors.

Also, in the case of the information terminal device 100 itself as illustrated in FIG. 5B, a display unit (100a or 100b) can be separated from an operation unit 100c provided with an operation button, a touch panel and the like so that the display unit can be switched between a larger one (large display 100b) and a smaller one (small display 100a) in accordance with the event of a competition and the measurement purpose. By this configuration, it is possible to appropriately give priority to either a sufficient information display capacity corresponding to the area of the display or power saving performance by miniaturizing the device size. Incidentally, in either case where the large display 100b or the small display 100a is selected and connected to the operation unit 100c, the information terminal device 100 can be mounted on the same belt member 104.

Each of the large display 100b and the small display 100a is provided with a liquid crystal display on top thereof, an engagement structure and an electrically connecting connector for connecting the display to the operation unit 100c on a side surface. The bottom portions of the large display 100b, the small display 100a and the operation unit 100c are provided with an engagement structure for mounting on the belt member 104. The belt member 104 is a member for putting the information terminal device 100 on an arm, and can be one of a variety of belt members in accordance with the use, i.e., a metal belt, a rubber belt, a leather belt, a nylon belt or the like.

The large display 100b or the small display 100a is connected to the operation unit 100c in an inclined fashion. After connection, the information terminal device 100 is curved in a dog leg form as seen from the side to conform to the roundness of an arm of a wearer. The large display 100b or the small display 100a is a display on which a message, an input string and the like are displayed to a user, and provided with a touch panel integrally formed on the upper surface side thereof. This touch panel detects a position touched of the display, for example, in units of dots forming the display by a detection system of a pressure-sensitive type, an optical type, an electrostatic type, an electromagnetic induction type or the like type to output a signal indicative of the detected position (hereinafter referred to as "touch position"). The touch position is represented by an XY coordinate system which is set as a coordinate system of the detection plane of the touch panel.

A user can perform various input operations by a touch operation on the display with a supplied touch pen, a finger or the like.

This touch panel, which is waterproofing, can detect a touched position of the display and outputs the detection signal as a touch position even on the surface of the water by a special electrostatic capacitance detection system. The touch position is represented by an XY coordinate system which is set as a coordinate system of the detection plane of the touch panel. A user can perform various input operations by a touch operation on the display even in an environment where water exists. Incidentally, the watch body can be operated also with mechanical buttons which are provided on the watch body.

Meanwhile, the small display 100a has an approximately trapezoidal shape having such a size as to fit into the width of the belt member 104. On the other hand, the large display 100b has a shape which is extending in the side direction from the width of the belt member 104. The extending portion is protruding in the arm direction toward the opposite side to the hand of the wearer.

The operation unit 100c is provided with a GPS antenna and a wireless antenna which are located in an external case. The GPS antenna is an antenna (first antenna) for wireless communication made of a conductive material such as a stainless steel for acquiring satellite information such as satellite orbit information, GPS time information, positional information and the like which are included in a navigation message of a satellite signal in a 1.5 GHz band extracted through a SAW filter which is not shown in the figure. Also, the wireless antenna incorporated in the operation unit 100c is an antenna for BTLE (Bluetooth (registered trademark) Low Energy), which are very low power consumption short range communication standards, and used for communicating with various sensors and other small devices worn on a body. This wireless antenna is made also of a conductive material such as a stainless steel.

Also, in the case of the present embodiment, the operation unit 100c is equipped with operation buttons for manually manipulating on the side surface thereof, and a touch panel, an LED for indicating a state or the like on the top surface of the operation unit 100c. Furthermore, in the case of the present embodiment, the operation unit 100c is waterproofing, and has the function to acquire and display speed information and positional information by processing radio waves (wireless signals) from a GPS satellite. Still further, an acceleration sensor or the like can be incorporated in the operation unit 100c to provide the functionality as an activity meter on the basis of the measurement of acceleration of body motions.

On the other hand, the docking type device 101b is an information terminal device which can be detachably connected to the information terminal device 100, and is a case body having a curved indent section which conforms to the profile of the information terminal device 100. In the case of the present embodiment, the docking type device 101b is made of a synthetic resin such as a cured plastic and provided with an information terminal device such as a CPU inside thereof. Then, in the case of the present embodiment, this docking type device 101b is formed with a dock side connection terminal (first connection terminal) 21 on the upper surface thereof, and detachably joined with the bottom portion of the external case of the information terminal device 100 through the dock side connection terminal.

Specifically, the bottom portion of the information terminal device 100 is provided with a terminal side connection terminal in a position corresponding to the dock side connection terminal so that the docking type device 101b and the information terminal device 100 can electrically be connected to each other by connecting the dock side connection terminal with the terminal side connection. The information terminal device 100 and the docking type device 101b are configured to supply electric power from the docking type device 101b to the information terminal device 100 through the dock side connection terminal, and transmit and receive data therebetween for displaying the data on the large display 100b or the small display 100a.

Also, this docking type device 101b is equipped with a battery which is detachable, has an RFID communication capability for contactlessly reading and writing data through wireless radio waves, and is capable of wirelessly communicating with an external reader writer with a wireless communication antenna provided on the docking type device 101b. This wireless antenna is an antenna for contactless wireless communication (NFC (Near Field Communication)) to transmit and receive data by the use of weak radio waves radiated from the external reader writer. Furthermore, in the case of the present embodiment, the docking type device 101b is provided with a USB terminal to be electrically connected to an external device such as a personal computer. The USB terminal is provided on the outside of the docking type device 101b as an external terminal to be connected to an external device through a USB cable, and installed in a connector which is located at one side of the docking type device 101b for protecting the USB terminal.

The power supply device 101c is a device detachably connected with the bottom portion of the docking type device 101b for supplying and charging electric power to the information terminal device 100 and the docking type device 101b. In the case of the present embodiment, the power supply device 101c may be an indoor installation type device to be installed in user's home or the like, or a portable device to be installed in an automobile or a bicycle. In the case where the power supply device 101c is an indoor installation type device, electric power is supplied through a wall outlet and a power cable. On the other hand, in the case where the power supply device 101c is a portable device, a battery may be provided which can accumulate power supply through an external AC adapter. Meanwhile, this battery may incorporate a transformer, a rectifier, a regulating circuit for converting an alternating current to a direct current. Incidentally, the configuration of the power supply device 101c can be modified in accordance to the use. For example, in the case where the power supply device 101c is installed on a table or the like, an installation base is provided on the bottom surface thereof. Also, in the case where the power supply device 101c is installed on a bicycle, an attachment member is attached for housing or fixing the power supply device 101c to a handlebar.

Next, the internal structure of the information terminal device 100 in accordance with the present embodiment will be explained. Specifically, as illustrated in FIG. 3, the information terminal device 100 is provided with a wireless interface 113, a control unit 170, a memory 114, an output interface 111 and an input interface 112.

More specifically, the information terminal device 100 in accordance with the present embodiment is provided with the function to collect detection results obtained by each body motion sensor 40, and obtains the detection results by a communication process between each motion sensor 40 and the wireless communication interface 113. The memory 114 of the information terminal device 100 serves as a body motion recording unit which can record the detection results of the body motion sensors 40 as body motion data. In this description, the body motion data is raw data detected by each of various sensors, and the body motion reproduction data is data which is obtained by recording and analyzing this body motion data, extracting necessary data, performing correction and so forth.

Incidentally, the detection results as transmitted from each body motion sensor 40 include sensor identification information which is added for identifying this each body motion sensor 40 and accumulated in the memory 114 of the information terminal device 100 so that when acquiring the detection result through the wireless communication interface 113, the control unit 170 can determine which body motion sensor 40 outputs that detection result. Also, this identification information of each sensor includes wearing part identification information for identifying the part on which this each sensor is worn, and body motion reproduction data can be calculated on the basis of this wearing part identification information. Furthermore, the body motion data includes time information when the detection result is acquired from each body motion sensor 40.

Incidentally, the information terminal device 100 is provided with the wireless interface 113 as a communication capability means. The wireless communication interface 113 is a module for controlling transmission and reception of various information through the communication network and controlling wireless short-range communication such as wifi or Bluetooth (registered trademark) to communicate with each body motion sensor 40 by the use of one of various protocols and perform data transmission and reception with the above server device and the like through 3G communication.

Furthermore, the information terminal device 100 is provided with the output interface 111 which displays or outputs an analysis result of body motion reproduction data, and display information generated by a display information generation unit 170e is displayed on the display 100a or 100b through the output interface 111.

Furthermore, the information terminal device 100 of the present embodiment has the function to analyze the body motions of a wearer on the basis of body motion data acquired from the sensors, and generate the body motion reproduction data. Specifically, as illustrated in FIG. 3, the information terminal device 100 is provided with the control unit 170 which is an arithmetic processing unit such as a CPU for performing arithmetic operations required for controlling the respective elements. Incidentally, the respective functions of the large display 100b are virtually implemented within the control unit 170 by running a motion capture program of the present invention with this control unit 170. More specifically, a body motion data acquisition unit 170a, a body motion calculation unit 170b, a cycle extraction unit 170c, an analysis unit 170d and a display information generation unit 170e are virtually implemented by running a motion capture application with the control unit 170.

The body motion data acquisition unit 170a is a module for acquiring body motion data from each body motion sensor 40 through the wireless interface 113. In the case of the present embodiment, the body motion data acquisition unit 170a acquires the body motion data as the detection result by performing wireless communication with each of the body motion sensor 40a through 41e. This body motion data is temporarily accumulated in the memory 114, and then the detection results of the body motion sensors 40 are transmitted to the body motion calculation unit 170b.

The body motion calculation unit 170b is a module for calculating body motions of a wearer as body motion reproduction data on the basis of the detection results of the body motion sensors 40a and 40b accumulated in the memory 114 (body motion recording unit) and the displacement, rotation and acceleration of the body motion sensors 40. In this case, the detection results of the body motion sensors 40 are values which are measured with a so-called nine-axis sensor and, in the case of the present embodiment, include the direction and magnitude of acceleration (including gravitational acceleration) of an object, an angular velocity (magnitude, direction and center position) of the object, and the direction (orientation) and magnitude of a magnetic field.

The body motions as calculated here include a factor indicative of the smoothness of pedaling, the angular velocity ω of the pedal shaft of a bicycle, the timely variation of this angular velocity ω, and the smoothness of the timely variation. Meanwhile, in the case of the present embodiment, the body motion sensors 40 are attached to right and left shoes so that the rotational motion that is detected by the sensors is the rotation of the shoes. However, when pedaling a bicycle, the shoes rotate on the pedal shaft so that ω is the angular velocity of this pedal shaft.

Furthermore, in the case of the present embodiment, this body motion calculation unit 170b is provided with the cycle extraction unit 170c. This cycle extraction unit 170c extracts a cyclic change contained in body motion on the basis of the body motion reproduction data accumulated in the memory 114. The cyclic change includes not only a simple circular motion but also three-dimensional complicated free orbital locuses C1 and C2 in which are combined wavelike motions and motions in the shape of a figure eight as illustrated in FIG. 2.

In the case of the present embodiment, the extracted orbital motions include an orbital motion C1a of the right foot body motion sensor 40a worn on the right instep of the wearer 1, and an orbital motion C1b of the left foot body motion sensor 40b worn on the left instep of the wearer 1. Each of the orbital motions C1a and C1b comprises a main orbital motion component in a plane xy defined by the vertical direction y and the direction x in which a wearer runs during running or a bicycle race. Incidentally, the analysis unit 170d has the function to analyze the pattern of an orbital motion to automatically determine the event of the competition which is currently practiced by extracting the characteristics of the orbital motion, and switch the settings of processes to the settings which are suitable for the event.

As a method of extracting this cyclic change, the following arithmetic operations are performed in the case of the present embodiment.

First, a rotation axis is estimated from values of the gyroscope in three axes in accordance with the following equation.

$$\text{Axis}=[\text{Gyro}X, \text{Gyro}Y, \text{Gyro}Z] \quad [\text{Eq. 1}]$$

Since the length of Axis is not 1, Normalization is performed to obtain the rotation axis (RotationAxis) by the following equation.

$$\text{RotationAxis}=\text{Axis·Normalize}( ) \quad [\text{Eq. 2}]$$

A rotation matrix QuatAxis is calculated by the following equation to indicate how much this RotationAxis is rotated in relation to the coordinates of the body of the wearer 1.

$$\text{QuatAxis}=\text{Quat}([X,Y,Z],\text{RotationAxis}) \quad [\text{Eq. 3}]$$

The rotation component with RotationAxis as a center can be extracted in the X-axis in accordance with the following equation by rotating body motion data detected by the body motion sensor 40 with this rotation matrix QuatAxis.

$$\text{RotatedGyro}=\text{ApplyQuat}([\text{Gyro}X,\text{Gyro}Y,\text{Gyro}Z],\text{QuatAxis})\text{MainComponentGyro}=\text{RotatedGyro·}X \quad [\text{Eq. 4}]$$

This MainComponentGyro is obtained as the angular velocity ω of the pedal shaft.

Meanwhile, in the case of the present embodiment, the body motion calculation unit 170b calculates the body motion of a wearer as body motion reproduction data on the basis of the detection result of the body motion sensors 40 and variation characteristic of orbital motions of the body motion sensors 40. In this case, for example, the body motion calculation unit 170b calculates three-dimensional free orbital locuses C1 of the body motion sensors 40 as illustrated in FIG. 2. Then, the body motion calculation unit 170b evaluates the collapse of orbital motions and the like in the left and right sides of the wearer on the basis of the calculated variation characteristic of the free orbital locuses C1(C1a and C1b). The body motion reproduction data is then calculated on the basis of the free orbital locuses C1 calculated in this manner.

The analysis unit 170d is a module for analyzing the body motion of the wearer 1 on the basis of body motion reproduction data. In the case of the present embodiment, the analysis unit 170d functions as a characteristic analysis unit which analyzes the characteristics of the angular velocity variation of cyclic motion extracted by the cycle extraction unit 170c. The characteristics analyzed here are displayed or output by an output device in correspondence with the rotation angle of the cyclic motion extracted by the cycle extraction unit 170c.

Figure 13A:
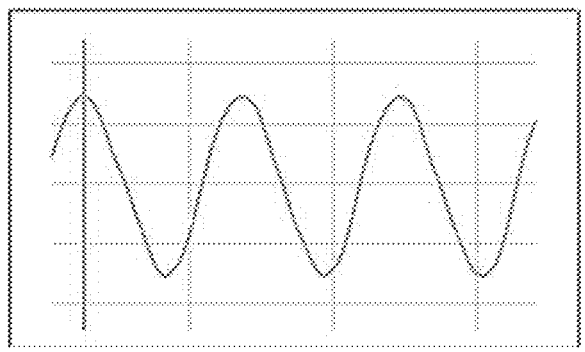
FIGS. 13A, 13B and 13C are explanatory views for showing an analysis method of body motion data in accordance with the embodiment.
Figure 13B:
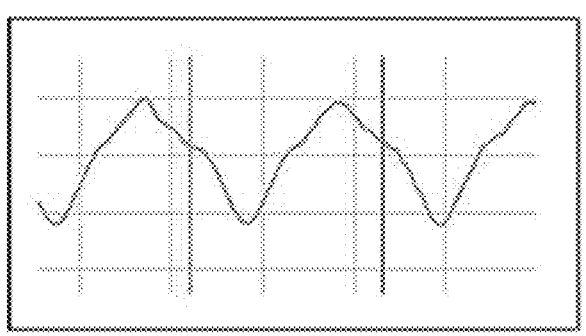
Figure 13C:
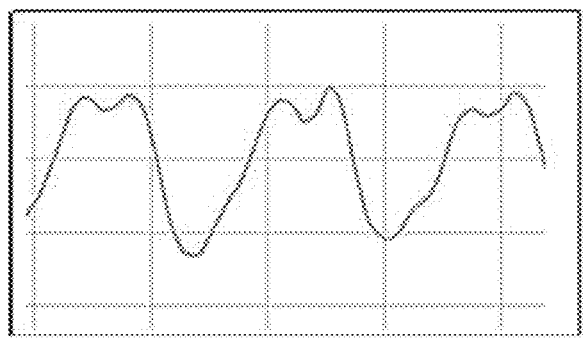
Figure 14A:
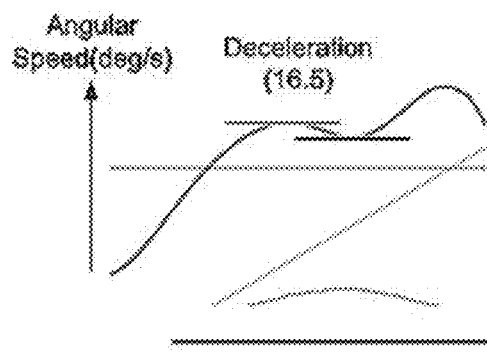
FIGS. 14A and 14B are explanatory views for showing an analysis method of body motion data in accordance with the embodiment.
Figure 14B:
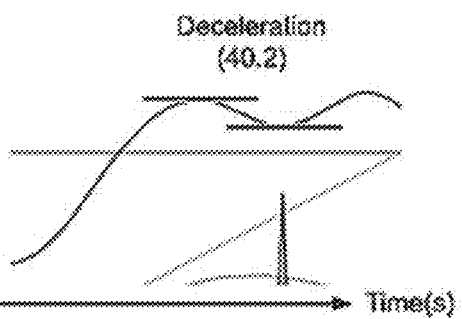

Specifically, the angular velocity ω of a pedal is generally known to have a waveform like a sine wave as illustrated in FIG. 13A, and this tendency is particularly noticeable in the case of proficient athletes. On the other hand, in the case of amateurs, tired athletes and the like, such a waveform tends to be deformed out of a smooth sine wave as illustrated in the same FIGS. 13B and 13C. In the case of the present embodiment, as illustrated in FIGS. 14A and 14B, the drop from a local maximum value to a local minimum value corresponding to deformation of a sine wave is used as a score to evaluate the characteristic of the angular velocity variation during the cyclic motion. In the case of the examples shown in FIGS. 14A and 14B, the score of example 14A is 16.5 and the score of example 14B is 40.2, so that the deformation of example 14B is evaluated as more significant.

In addition, the analysis unit 170d performs analysis to estimate the pedal position. While there is a factor to decelerate the angular velocity ω (MainComponentGyro) of a pedal someplace during rotation of the pedal crank, the pedal position is estimated by the use of the acceleration of the same sensor to provide the wearer 1 with the pedal position as the analysis result of the angular velocity variation characteristic. The crank of a bicycle generally rotates in the range of 30 rpm to 200 rpm. The length of the crank is usually about 160 mm to 180 mm so that, depending upon the position where the body motion sensor 40 is worn, the body motion sensor 40 rotates at about 100 rpm about 200 to 300 mm away from the center of rotation. In this case, the centrifugal force exerted on the sensor is expressed by the following equation as an ideal value.

$$\text{Centrifugal Force (m/s}^2\text{)}=r\omega^2 \approx 32.898 \text{ [m/s}^2\text{]}(r=300 \text{ mm}, \omega=100 \text{ rpm}) \quad [\text{Eq. 5}]$$

In accordance with this equation, the centrifugal force as exerted is three times the acceleration of gravity. Even if the rotational speed is 30 rpm, a centrifugal force of the acceleration of gravity is exerted. In this condition, the vector length measured by a three-axis acceleration sensor indicates a minimum value near the top dead center of the pedal where the centrifugal force and the acceleration of gravity are canceled each other, and a maximum value near the bottom dead center of the pedal where the centrifugal force and the acceleration of gravity are added together.

The vector length is simply calculated by the following equation, and the pedal position can be estimated by linear interpolation between the maximum value as the bottom dead center and the minimum value as the top dead center.

$$AccLength=\sqrt{(AccX^2+AccY^2+AccZ^2)} \quad [Eq. 6]$$

Incidentally, as another analysis method by this analysis unit 170d, stereoscopic image data is generated to three-dimensionally display the wearer 1, or improvement data indicative of the difference from a normal body motion is generated for example by extracting model body motion data from the memory 114 storing such model body motion data and comparing the body motion reproduction data of the wearer with the model body motion data. Furthermore, by registering user information in advance such as gender, height, weight and age, analysis may be performed on the basis of the user information. Then, the analysis unit 170d transmits the analysis result such as this stereoscopic image data and improvement data to the information terminal device 100.

Figure 8A:
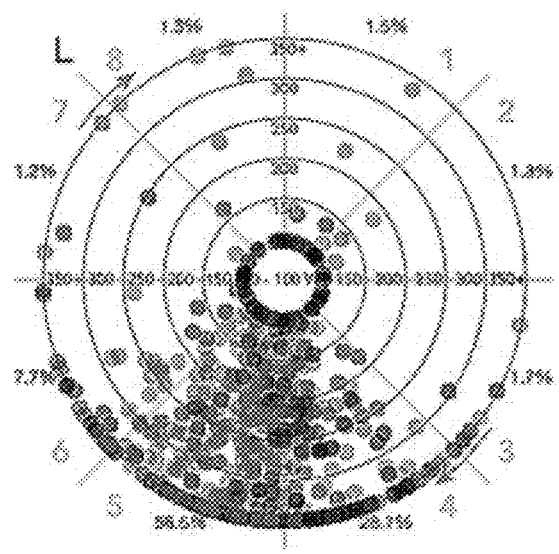
FIGS. 8A, 8B and 8C are screen configuration views showing the display screen of the motion capture system in accordance with the embodiment.
Figure 8B:
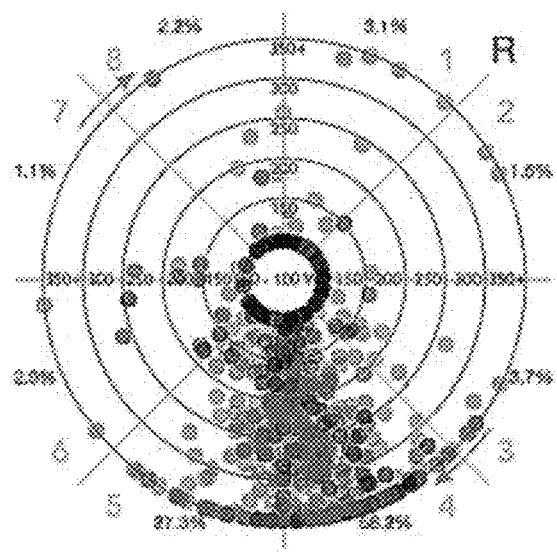
Figure 8C:
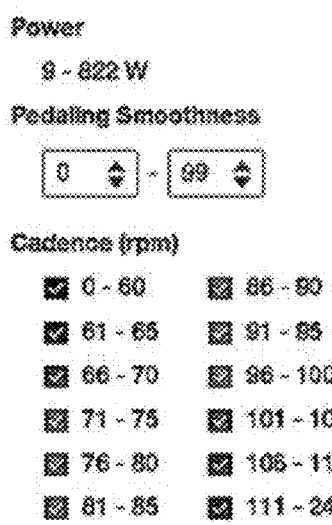

The display information generation unit 170e is a module for generating display information to be displayed through the output interface 111, and generates display information to be displayed and output by associating the characteristics analyzed by the analysis unit 170d with the rotation angle of the cyclic motion extracted by the cycle extraction unit 170c. In the case of the present embodiment, as illustrated in FIGS. 8A to 8C, this display information is provided to display a plane circle as the cyclic motion extracted by the cycle extraction unit 170c, display a central angle of this plane circle as the rotation angle at which the characteristic of the cyclic motion analyzed by the analysis unit 170d appears, express the strength of each characteristic of the cyclic motion by the distance from the origin of the plane circle, and express the variation of each characteristic of the cyclic motion by a symbol, a figure and the color or size thereof. Meanwhile, this display information includes a sound signal and other output control signals together with display data.

The memory 114 is a storage unit for storing various data such as the identification information for identifying each information terminal device 100, the wearing part identification information of each body motion sensor 40, the relative positional relationship of the body motion sensors 40 worn on the respective positions, the user information, the model body motion data and the like.

(Motion Capture Method)

Figure 7:
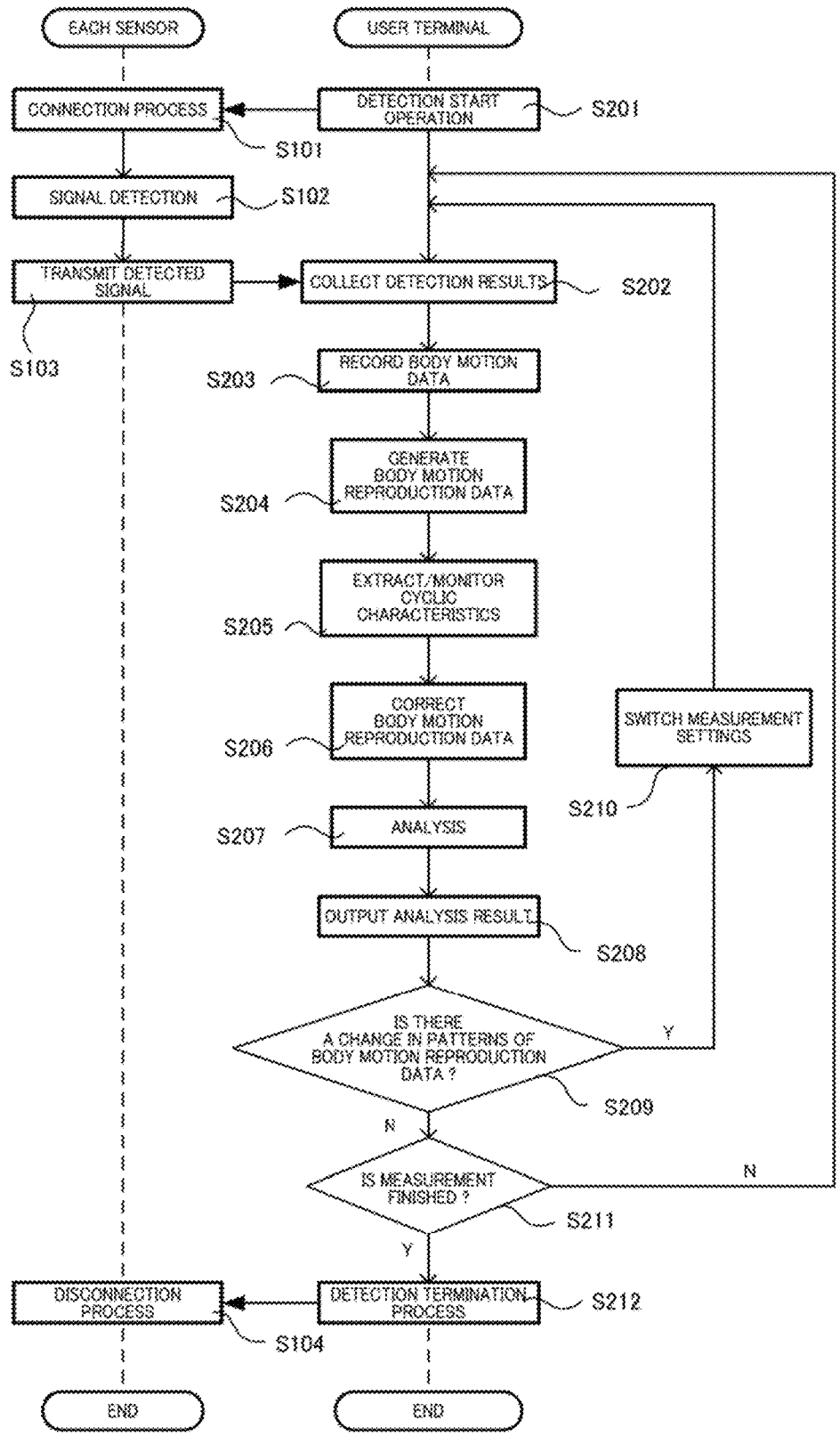
FIG. 7 is a sequence diagram for showing the motion capture method in accordance with the embodiment.

The motion capture method in accordance with the present invention can be implemented by operating the motion capture system having the structure as described above. FIG. 7 is a sequence diagram for showing the motion capture method in accordance with the present embodiment. Meanwhile, in this case, this example is explained in the case where coaching is conducted for bicycle race.

First, the wearer 1 wears the body motion sensors 40a and 40b on both feet. Also, the wearer 1 performs motion capture by fixing the information terminal device 100 to the handlebar 102 of a bicycle through the mount device 101 and the docking type device 101b and charging the information terminal device 100 from the power supply device 101c through the docking type device 101b.

When fixing of the information terminal device 100 is completed, the information terminal device 100 is then operated in order to acquire the detection results from the sensors 40 (S201). In this case, while a competition item can be select by user operation, it is also possible to switch the process settings to settings suitable for the competition item by extracting the characteristics of the orbital motion as described above and automatically determining the preset event of the competition from the extracted pattern. By this function, it is possible to seamlessly continue measurement without a need for particular operation even when the competition item is switched in the middle.

The control unit 170 of the information terminal device 100 acquires an operation signal in response to the operation for starting detection, and then performs a connection process with each body motion sensor 40 (S101). After performing the connection process, each motion sensor 40 detects the motion of the wearer 1. Specifically, three-dimensional displacements or accelerations at each part of the wearer are detected by the body motion sensor 40 worn on this each part (S102). Then, the detection results which are acquired are transmitted to the wireless interface 113 of the information terminal device 100 from the wireless communication unit of each body motion sensor 40 by using weak electric waves (S103). When the wireless interface 113 of the information terminal device 100 acquires the detection results (S202), the memory 114 serving as a body motion recording unit stores the detection results of the body motion sensors 40a and 40b as body motion data (S203).

Thereafter, after the body motion data acquisition unit 170a acquires the body motion data, the cycle extraction unit 170c transmits the detection results of the body motion sensor 40 to the body motion calculation unit 170b. The body motion calculation unit 170b calculates body motions of the wearer as body motion reproduction data on the basis of the detection results of the body motion sensors 40 accumulated in the body motion recording unit and the relative positional relationship among the body motion sensors 40 (S204), and transmits the body motion reproduction data to the analysis unit 170d. On the other hand, when a predetermined cycle arrives on the basis of the detection results of the cycle extraction unit 170c, the analysis unit 170d corrects the body motion reproduction data calculated by the body motion calculation unit 170b (S206).

Furthermore, the analysis unit 170d analyzes the body motion of the wearer on the basis of the body motion reproduction data (S207). The analysis result data is displayed in the display 100a or 100b or output through a speaker by sound (S208). Incidentally, when a change is detected in the patterns of the extracted orbital motion and body motion reproduction data ("Y" in S209), the event of the competition which is currently taking place is automatically determined with reference to the patterns to switch over to measurement settings suitable for the competition event (S210).

The above process is continuously performed during competition ("N" in S211), and, the communication with the sensors are terminated (S212 and S104) as soon as the detection process is finished ("Y" in S211).

(Motion Capture Program)

Incidentally, the motion capture system and the motion capture method in accordance with the present invention as described above can be implemented in a computer by running the motion capture program of the present invention described in a predetermined language is the same as the above described motion capture application. Namely, the system having the functionality as described above can be built to implement the motion capture method by installing the program of the present invention in an IC chip or a memory device of a mobile terminal device, a smartphone, a wearable terminal, a mobile PC, another type information processing terminal, or a general purpose computer such as a personal computer or a server computer, and running the program on the CPU.

(Effect/Action)

In accordance with the present embodiment as discussed above, it is possible to instantaneously comprehend the occurrence of the disturbance of a form and the collapse of a rhythm when stepping on the pedal of a bicycle by detecting a cyclic motion such as pedaling a bicycle and associating the rotation angle with the characteristics of the cyclic motion.

Particularly, in the case of the above invention, the body motion sensor can be located on a footwear such as an athletic shoe which is worn below an ankle so that the body motion sensor can be worn together with the footwear, and therefore the body motion sensor can easily be worn. In addition, since the body motion sensor can be freely worn in an arbitrary position and an arbitrary direction, usability can be improved.

Furthermore, as illustrated in FIGS. 8A to 8C, the output device displays a plane circle as the cyclic motion extracted by the cycle extraction unit, and displays a central angle of this plane circle as the rotation angle at which the characteristic analyzed by the characteristic analysis unit appears, and therefore it is possible to geometrically express cyclic motions in accordance with the rotation angles thereof and comprehend the characteristics of the cyclic motions at first sight.

Also, the motion capture program in accordance with the present embodiment can be distributed, for example, through a communication line, or as a package application which can be run on a stand-alone computer by storing the program in a storage medium which can be read by a computer. Specifically, such a storage medium includes a magnetic recording medium such as a flexible disk or a cassette tape, an optical disc such as CD-ROM or DVD-ROM, a RAM card and a variety of storage mediums. In addition, in accordance with the computer readable medium in which this program is stored, the above system and method can be easily implemented with a general purpose computer or a dedicated computer, and the program can be easily maintained, transported and installed.

DESCRIPTION OF REFERENCE SIGNS

C1 . . . free orbital locus
x . . . moving direction
y . . . vertical direction
1 . . . wearer
40 . . . body motion sensor
40a . . . right foot body motion sensor
40b . . . left foot body motion sensor
41 . . . indent section
41a . . . flange portion
42 . . . gripping member
42a, 42b . . . cut portion
43 . . . stopper
44 . . . main body frame
44a . . . connection member
44b . . . engagement hole
51 . . . shoelace
100 . . . information terminal device
100a . . . small display
100b . . . large display
100c . . . operation unit
101 . . . mount device
101b . . . docking type device
102 . . . handlebar
104 . . . belt member
111 . . . output interface
112 . . . input interface
113 . . . wireless interface
114 . . . memory
170 . . . control unit
170a . . . body motion data acquisition unit
170b . . . body motion calculation unit
170c . . . cycle extraction unit
170d . . . analysis unit
170e . . . display information generation unit

What is claimed is:

1. A motion capture system which detects body motions of a wearer comprising:
a plurality of body motion sensors which are worn on parts of the body of the wearer, which are cyclically moved, so that three-dimensional displacement and acceleration of each of the parts can be measured;
a body motion recording unit which records detection results of the body motion sensors as body motion data;
a cycle extraction unit which extracts a cyclic motion of each of the body motion sensors on the basis of the body motion data accumulated in the body motion recording unit;
a characteristic analysis unit which analyzes a characteristic of angular velocity variation of the cyclic motion extracted by the cycle extraction unit;
an output device which displays or outputs the characteristic analyzed by the characteristic analysis unit in correspondence with a rotation angle of the cyclic motion extracted by the cycle extraction unit, wherein
the characteristic analysis unit has a function to analyze a pattern of the cyclic motion, extract the characteristic of the cyclic motion, determine an event of a competition which is currently practiced by the wearer, and switch settings of processes to suitable settings for the event that is determined,
the body motion sensors incorporate a three-axis acceleration meter for measuring the acceleration of each of the parts, a three-axis gyroscope for measuring an angular speed of each of the parts, and a three-axis magnetic sensor for measuring a magnitude and direction of a magnetic field, and
the characteristic analysis unit estimates the position of a pedal as a minimum value near a top dead center of the pedal where a centrifugal force and the acceleration of gravity are canceled each other, and a maximum value near a bottom dead center of the pedal where a centrifugal force and the acceleration of gravity are added together.

2. The motion capture system as recited in claim 1 wherein
the body motion sensors are worn on parts located below both ankles of the wearer, and wherein
the characteristic analysis unit evaluates a drop from a local maximum value to a local minimum value corresponding to deformation of a sine wave, which is indicative of the angular velocity of a cyclic motion of the pedal, as a score of the characteristic of the angular velocity variation.

3. The motion capture system as recited in claim 1 wherein
the output device displays a plane circle as the cyclic motion extracted by the cycle extraction unit, and displays a central angle of this plane circle as the rotation angle at which the characteristic analyzed by the characteristic analysis unit appears.

4. The motion capture system as recited in claim 3 wherein
the output device displays the strength of the characteristic detected by the body motion sensor in correspondence with the distance from the origin of the plane circle.

5. The motion capture system as recited in claim 3 wherein
the output device displays the variation of the characteristic detected by the body motion sensor with a symbol, a figure and a color or size thereof.

6. A motion capture program for detecting body motions of a wearer, causing an information processing terminal to function as:
a plurality of body motion sensors which are worn on parts of the body of the wearer, which are cyclically moved, so that three-dimensional displacement and acceleration of each of the parts can be measured;
a body motion recording unit which records detection results of the body motion sensors as body motion data;
a cycle extraction unit which extracts a cyclic motion of each of the body motion sensors on the basis of the body motion data accumulated in the body motion recording unit;
a characteristic analysis unit which analyzes a characteristic of angular velocity variation of the cyclic motion extracted by the cycle extraction unit;
an output device which displays or outputs the characteristic analyzed by the characteristic analysis unit in correspondence with a rotation angle of the cyclic motion extracted by the cycle extraction unit, wherein
the characteristic analysis unit has a function to analyze a pattern of the cyclic motion, extract the characteristic of the cyclic motion, determine an event of a competition which is currently practiced by the wearer, and switch settings of processes to suitable settings for the event that is determined,
the body motion sensors incorporate a three-axis acceleration meter for measuring the acceleration of each of the parts, a three-axis gyroscope for measuring an angular speed of each of the parts, and a three-axis magnetic sensor for measuring a magnitude and direction of a magnetic field, and
the characteristic analysis unit estimates the position of a pedal as a minimum value near a top dead center of the pedal where a centrifugal force and the acceleration of gravity are canceled each other, and a maximum value near a bottom dead center of the pedal where a centrifugal force and the acceleration of gravity are added together.

7. The motion capture program as recited in claim 6 wherein
the body motion sensors are worn on parts located below both ankles of the wearer, and wherein
the characteristic analysis unit evaluates a drop from a local maximum value to a local minimum value corresponding to deformation of a sine wave, which is indicative of the angular velocity of a cyclic motion of the pedal, as a score of the characteristic of the angular velocity variation.

8. The motion capture program as recited in claim 6 wherein
the output device displays a plane circle as the cyclic motion extracted by the cycle extraction unit, and displays a central angle of this plane circle as the rotation angle at which the characteristic analyzed by the characteristic analysis unit appears.

9. The motion capture program as recited in claim 8 wherein
the output device displays the strength of the characteristic detected by the body motion sensor in correspondence with the distance from the origin of the plane circle.

10. The motion capture program as recited in claim 8 wherein
the output device displays the variation of the characteristic detected by the body motion sensor with a symbol, a figure and a color or size thereof.

11. A motion capture method which detects body motions of a wearer comprising:
a body motion recording step of measuring, with body motion sensors which are worn on parts of the body of the wearer which are cyclically moved, three-dimensional displacement and acceleration of each of the parts, and recording detection results of the body motion sensors as body motion data;
a cycle extraction step of extracting, with a period extraction unit, a cyclic motion of each of the body motion sensors on the basis of the body motion data accumulated in the body motion recording unit;
a characteristic analysis step of analyzing, with a characteristic analysis unit, a characteristic of angular velocity variation of the cyclic motion extracted in the cycle extraction step; and
an output step of displaying or outputting the characteristic analyzed in the characteristic analysis step through an output device in correspondence with a rotation angle of the cyclic motion extracted by the cycle extraction unit, wherein
in the characteristic analysis step, the characteristic analysis unit analyzes a pattern of the cyclic motion, extracts a characteristic of the cyclic motion, determines an event of a competition which is currently practiced by the wearer, and switches settings of processes to suitable settings for the event that is determined,
the body motion sensors incorporate a three-axis acceleration meter for measuring the acceleration of each of the parts, a three-axis gyroscope for measuring an angular speed of each of the parts, and a three-axis magnetic sensor for measuring a magnitude and direction of a magnetic field, and
the characteristic analysis unit further estimates the position of a pedal as a minimum value near a top dead center of the pedal where a centrifugal force and the acceleration of gravity are canceled each other, and a maximum value near a bottom dead center of the pedal where a centrifugal force and the acceleration of gravity are added together.

12. The motion capture method as recited in claim 11 wherein
in the measuring/recording step, the body motion sensors are worn on parts located below both ankles of the wearer who is pedaling a bicycle, wherein
in the characteristic analysis step, the characteristic analysis unit further evaluates a drop from a local maximum value to a local minimum value corresponding to deformation of a sine wave, which is indicative of the angular velocity of a cyclic motion of the pedal, as a score of the characteristic of the angular velocity variation.

13. The motion capture method as recited in claim 11 wherein in the output step, the output device displays a plane circle as the cyclic motion extracted by the cycle extraction unit, and displays a central angle of this plane circle as the rotation angle at which the characteristic analyzed by the characteristic analysis unit appears.

14. The motion capture method as recited in claim 13 wherein in the output step, the output device displays the strength of the characteristic detected by the body motion sensor in correspondence with the distance from the origin of the plane circle.

15. The motion capture method as recited in claim 13 wherein in the output step, the output device displays the variation of the characteristic detected by the body motion sensor with a symbol, a figure and a color or size thereof.

* * * * *